United States Patent [19]
Satou et al.

[11] 4,291,986
[45] Sep. 29, 1981

[54] OPTICAL RATE ASSAY APPARATUS

[75] Inventors: Takehide Satou, Katsuta; Kasumi Yoshida, Mito; Hisayuki Sagusa, Katsuta; Osamu Ohno, Katsuta; Tetuaki Abe, Katsuta, all of Japan

[73] Assignee: Hitachi, Ltd., Tokyo, Japan

[21] Appl. No.: 62,115

[22] Filed: Jul. 30, 1979

[30] Foreign Application Priority Data

Dec. 14, 1978 [JP] Japan .................. 53-153657

[51] Int. Cl.³ .......................................... G01N 21/85
[52] U.S. Cl. .................... 356/410; 356/440; 422/67
[58] Field of Search .............. 356/409, 410, 411, 414, 356/436, 440; 422/67

[56] References Cited

U.S. PATENT DOCUMENTS

| | | | |
|---|---|---|---|
| 3,319,512 | 5/1967 | Isreeli | 356/410 |
| 3,728,080 | 4/1973 | Moran | 422/67 |
| 3,948,607 | 4/1976 | Atwood et al. | 422/63 |
| 4,021,123 | 5/1977 | Atwood et al. | 356/244 |

*Primary Examiner*—Vincent P. McGraw
*Attorney, Agent, or Firm*—Craig and Antonelli

[57] ABSTRACT

A serum and a reagent are supplied into a reaction tube to prepare a reactive solution or a sample solution which is sucked up at a predetermined position into one of a plurality of flow cells. The flow cells are mounted on a thermostatic block to be heated to a predetermined temperature and alternatively supplied with the sample solution. After a sample solution has been introduced from a specified reaction tube into one of the flow cells and heated to the predetermined temperature, the sample solution in the one flow cell is irradiated with light to measure changes in absorbance of the sample solution for a predetermined time. During a period when the absorbance changes of the sample solution in one flow cell is measured, another sample solution is introduced from another reaction tube into another flow cell and heated to the predetermined temperature. Immediately after the measurement of the absorbance changes of the sample solution in the one flow cell has been completed, the other flow cell is irradiated with light to measure the changes in absorbance of the sample solution in the other flow cell. Thereafter, one and the other flow cells are alternately supplied with a sample solution to successively measure the absorbance changes. Thus, a waiting time for stabilizing the temperature of the sample solution introduced into the flow cell can be actually dispensed with, and therefore effective measurement can be made.

10 Claims, 4 Drawing Figures

OPTICAL RATE ASSAY APPARATUS

BACKGROUND OF THE INVENTION

The present invention relates to an apparatus for analyzing liquid samples, and more particularly to a liquid sample analizing apparatus suitable for use in measuring optical characteristics of a liquid sample which is prepared by mixing a material to be examined with a reactive reagent in a reaction tube and then introduced into a flow cell.

Recently, the rate assay method (hereinafter referred to as the rate method) has been extensively employed in the field of clinical biochemical analysis. The rate method is fundamentally small in endogenous error, and therefore superior in accuracy of measured value to the colorimetric measurement. On the other hand, the rate method has a drawback that the measured value is readily affected by the temperature of sample solution under measurement. For the above reason, in a practical analizing apparatus, it is required to rapidly heat or cool a sample solution to a constant temperature, and to maintain it at the constant temperature during the rate measurement. The rate method may be carried out with such an analizing apparatus as disclosed in U.S. Pat. No. 3,728,080. In such an analyzing apparatus, a sample solution is introduced from a reaction tube into a flow cell to permit observation of absorbance change depending on the sample solution. According to the rate method, the sample solution is held in the flow cell for a predetermined period of time so that the absorbance of the sample solution is measured a plurality of times to obtain changes in absorbance at the predetermined period of time, resulting in a lower speed for sample processing in the rate method than in the colorimetric measurement.

In conventional analizing apparatus for rate assay, a sample solution is introduced from a reaction tube into a single flow cell, and after the photometric operation for rate assay has been completed, a different sample solution is introduced from a next reaction tube into the same flow cell to conduct a next rate assay. In such an analising apparatus using a single flow cell, when transferred from the reaction tube to the flow cell, the sample solution is cooled by the air to a temperature which is lower than a temperature required in measuring the absorbance. Therefore, prior to the photometric operation, thus an operator has to wait for a while until the temperature of the sample solution in the flow cell is increased to reach a predetermined value. That is, the time taken to measure one sample solution with the conventional apparatus is equal to the sum of the time for temperature stabilization and the time for rate measurement (or photometric operation), so that this sum determines the sample processing speed in the conventional apparatus.

A plurality of flow cells are employed in the present invention. The use of two flow cells is not novel and one of the two flow cells is used for a sample solution while the other for a reference solution to compare two photometric signals resulting from the sample and reference solutions so as to define a measured value based upon the comparison in such a conventional photometer utilizing two flow cells. As will be clarified later, the function of a plurality of flow cells employed in the present invention is entirely different from the function of those used in the conventional photometer.

SUMMARY OF THE INVENTION

It is an object of the present invention to provide an analizing apparatus for liquid samples in which the sample processing capability in rate assay is greatly improved.

It is another object of the present invention to provide an analizing apparatus for liquid samples in which preparations are made for the measurement of a next sample solution in a period when a previous or preceding sample solution is subjected to the rate assay, and thus the rate assay of the next sample can be started without any waiting time.

It is a further object of the present invention to provide an analizing apparatus for liquid samples in which the temperature of a sample solution can be stabilized in a flow cell prior to rate assay, to achieve a high accuracy of measurement.

A principal feature of the present invention is that an apparatus for analyzing liquid samples comprises a train of vessels each containing a sample solution whose optical characteristic is to be measured; a plurality of flow cells; means for maintaining the flow cells at a constant temperature; means for introducing, during a period when a sample solution introduced from a specified one of the vessels into a specified one of the flow cells is held in the specified flow cell, another sample solution contained in a next one of the vessels into a different one of the flow cells; fluid passage blocking means which operates in a manner so that, during the period when the sample solution introduced from the specified vessel into the specified flow cell is held in the specified flow cell, a fluid transferring passage for causing the sample solution in said next vessel to pass through the different flow cell is blocked, after it has been once opened when a sample solution is introduced into the different flow cell, so as to stop the transfer of the sample solution in the different flow cell in order to raise the temperature of the sample solution in the different flow cell to the constant temperature prior to irradiation of the sample solution with light; optical unit means for observing changes in absorbance of the sample solution in the different flow cell by irradiating the sample solution in the different flow cell with light, after changes in absorbance of the sample solution in the specified flow cell has been observed; and means for displaying results of observation corresponding to the respective absorbance changes of the sample solutions introduced into the specified and different flow cells, whereby the optical characteristic measurement of the sample solution in the specified cell can be immediately followed by the optical characteristic measurement of the sample solution in the different flow cell.

In an automatic discrete-type analizing apparatus for rate assay according to a preferred embodiment of the present invention, a train of reaction tubes are intermittently moved, and a plurality of flow cells are disposed apart from the train of reaction tubes. Further, during a period when a photometric operation is conducted for one flow cell, another flow cell sucks up a reactive solution or sample solution from a reaction tube to previously maintain the sample solution at a constant temperature. Immediately after the photometric operation for the one flow cell has been completed, the other flow cell is placed on the optical axis of a photometer in place of the one flow cell so that, absorbance changes of the sample solution which has been sucked into the other flow cell and maintained at the constant temperature, is observed.

In the preferred embodiment of the present invention, means for introducing a sample solution from a reaction tube into a flow cell is made up of a suction pipe for sucking the sample solution, a vertical movement mechanism for putting the suction pipe in and out of the reaction tube, and a syringe mechanism for sucking and discharging the sample solution. The introducing means are not limited to the above-mentioned, but may be constructed in such a manner that each of the reaction tubes is provided at its bottom with a pipe for discharging the sample solution and the pipe is connected with the flow cell through a passage changeover valve. Further, in the preferred embodiment, such a suction pump as applying a negative pressure to the exit side of the flow cell is employed in order to transfer the sample solution. However, the transfer of the sample solution may be effected in such a manner that the inside of a hermetically sealed reaction tube is applied with a positive pressure by a pressure device so that the sample solution is transferred due to a pressure difference between the tube and the flow cell. Furthermore, in the preferred embodiment, an optical path from a light source is fixed and a plurality of flow cells are successively placed on the optical path. However, another arrangement may be employed in which a plurality of flow cells are fixed and the optical path is successively directed to respective flow cells by mirror means or the like.

DESCRIPTION OF THE PREFERRED EMBODIMENT

Figure 1:
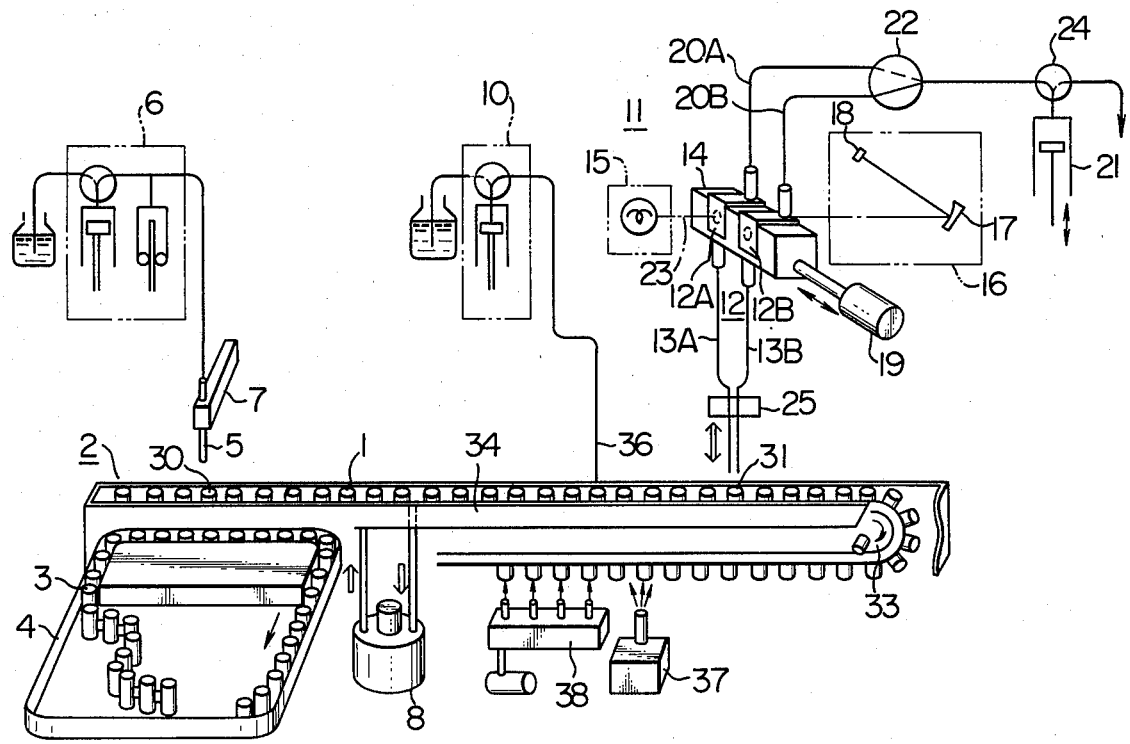
FIG. 1 is a schematic view of an embodiment of an analizing apparatus for liquid samples according to the present invention.

Referring to FIG. 1 which shows in brief the construction of an embodiment according to the present invention, a reaction line 2 is provided at both ends with sprockets 33 and at its upper portion with a heating bath 34 for dipping reaction tubes 1 therein. A multiplicity of reaction tubes 1 are supported by an endless chain, and transferred intermittently by means of the sprockets 33. Thus, a train of reaction tubes are formed. Although a plurality of trains of reaction tubes are employed in an actual apparatus, only a single train of reaction tubes are shown herein for the sake of simplicity. In a sampler 4, a plurality of sample cups 3 which contain therein serum as a material to be examined or a sample, are connected with each other by bendable chains and transferred intermittently in such a manner that each sample cup can pass through a sampling position. A nozzle 5 for sucking a sample solution is connected to a pipet mechanism 6 which includes a syringe for sucking and discharging the sample solution and another syringe for sucking and discharging a reagent solution. When a sample cup 3 reaches the sampling position of the sampler 4, the nozzle 5 is inserted into the sample cup 3 by means of a nozzle moving mechanism 7. The serum is sucked into the nozzle 5 by the action of the pipet mechanism 6 and held in the nozzle 5. Then, the nozzle 5 is moved by means of the nozzle moving mechanism 7 to a discharging position 30 of the reaction line 2 and the serum held in the nozzle 5 is discharged into a reaction tube 1 placed at the discharging position 30. Successively, a first reagent solution suited to an examination item is discharged from the nozzle 5 into the reaction tube 1 to dilute the serum. Then, the reaction tube 1 is transferred to a predetermined position as it is dipped in the heating bath 34 which is maintained at a constant temperature. When the reaction tube 1 reaches the predetermined position, a second reagent solution is supplied through a nozzle 36 into the reaction tube 1 by a dispensation mechanism 10, so that reaction proceeds between the serum and the reagent solutions in the reaction tube 1 under the constant temperature which is maintained by the heating bath 34. The reaction tube 1 in consideration is further transferred to a sucking position 31 of the reaction line 2 at which the sample solution in the reaction tube 1 is sucked up into a flow cell 12 of a photometer 11 to measure changes in absorbance of the sample solution in which the reaction is proceeding between the serum and the reagent solutions. The absorbance changes measured by the photometer 11 is indicated as measured values through a predetermined electric circuit.

The reaction tube 1 is turned upside down at the position of the sprocket 33 to discharge the remaining sample solution therein and then further transferred under the upside-down condition on the lower portion of the reaction line 2. After being sprayed with a cleaning solution by a cleaning unit 37, the reaction tube 1 is dried by warm air from a drying unit 38 and then returned in a clean state to the discharging position 30 to be used again. The constant-temperature water in the heating bath 34 is supplied from a circulating thermostat 8.

In this embodiment, two flow cells 12A and 12B are provided for one reaction line and mounted on a thermostat 14 equipped with a Peltier element. The flow cells 12A and 12B are connected on their entrance side to flexible suction pipes 13A and 13B at their one ends, respectively. Other ends of the suction pipes 13A and 13B each in the form of a vertical nozzle are moved by a vertical movement mechanism 25 in such a manner that the suction pipes 13A and 13B are selectively alternatively inserted into a reaction tube 1 or both of the suction pipes 13A and 13B are simultaneously inserted into a reaction tube 1. The flow cells 12A and 12B and the thermostat 14 are united into a block. The block is moved by a cell moving mechanism 19, which is formed of an air cylinder mechanism or a reciprocation mechanism including a cam and a motor, so that the flow cells 12A and 12B are alternately placed on an optical path from a lamp 15 at predetermined time intervals. Light travelling along an optical axis 23 is led into a spectrometer 16 so that it is separated into wavelength components by a dispersion element 17 disposed in the spectrometer 16 and converted into an electric signal by a photodetector 18 placed at a position corresponding to a specified wavelength. The flow cells 12A and 12B are connected on their exit side with pipes 20A and 20B which are connected to a passage change-over valve 22. The valve 22 blocks a passage corresponding to a flow cell for which the optical characteristics or the absorbance changes are being measured so as to stop the movement of the sample solution in the flow cell. When the sample solution is introduced into a flow cell, the passage change-over valve 22 is so set as to make a suction pump 21 communicate with one of the pipes 20A and 20B and the piston of the suction pump 21 is moved to conduct a sucking operation. So long as the operation of the suction pump 21 is stopped, the sample solution in a flow cell is never transferred due to the blocking of a change-over valve 24 even though the passage for the flow cell is open. In order to introduce a sample solution in a reaction tube into a flow cell, the vertical movement mechanism 25 for suction pipe, the passage change-over valve 22, the change-over valve 24 and the suction pump 21 are operated in cooperation. The passage change-over valve 22 determines which of the flow cells 12A and 12B is to be supplied with the sample solution. After being introduced into the selected flow cell, the sample solution is held for a while in the flow cell to be thermally stabilized to a constant temperature. The valves 22 and 24 act to block the sample solution passage to held the sample solution in the flow cell.

In such a state that the suction pump 21 communicates with the suction pipe 13A through the passage change-over valve 22, the pipe 20A, and the flow cell 12A and, at the same time, that the flow cell 12B is placed on the optical axis 23 while without placing the flow cell 12A on the same optical axis, a reaction tube 1 containing a next sample solution in which reaction is proceeding is transferred to the sucking position 31 beneath the suction pipe 13A. Then, the suction pipe 13A is inserted into the reaction tube 1 and then the suction pump 21 is driven to suck up the sample solution into the flow cell 12A. The thus sucked sample solution is held in the flow cell 12A without being moved. Since the suction pipe 13A is disposed in contact with the open air, the sample solution which has been maintained at a constant temperature by the heating bath 34 is subject to a temperature change when sucked up into the flow cell 12A. The sample solution, however, may be once more maintained at a constant temperature by the thermostat 14. According to the inventors' experiments, in a case where the reaction tube and the flow cell are both maintained at a temperature of 37° C., that a tetrafluoroethylene tube having a length of 50 cm and a diameter of 0.8 mm is employed as the suction pipe 13, and the ambient temperature is equal to 20° C., the sample solution is subject to a temperature fall of about 1.5° C. when sucked up into the flow cell under the condition of ambient temperature of 20° C. It takes about 20 seconds for the sample solution to be heated again to 37°±0.05° C. in the flow cell made of pyrex glass.

When the desired rate measurement on the preceding sample solution has been completed and the sample solution in the flow cell 12A has been heated to the constant temperature, the flow cell 12A is placed on the optical axis 23 by the cell moving mechanism 19 to observe the changes in absorbance of the sample solution in the flow cell 12A for a predetermined time, which is usually made equal to about 20 seconds in view of the stability of the photometer. The reaction rate is calculated based on the rate of absorbance change per unit time so as to obtain an active value of a constituent (to be examined) contained in the serum.

While, in a period when the rate measurement is carried out for the sample solution in the flow cell 12A, the passage change-over valve 22 is changed over to connect the suction pump 21 to the suction pipe 13B through the pipe 20B and the flow cell 12B and the train of reaction tubes in the reaction line 2 are transferred or moved by one step to place a next reaction tube which follows the reaction tube which had previously contained the sample solution held now in the flow-cell 12A at the position 31 beneath the suction pipe 13B. In this state, the suction pipe 13B is inserted into the reaction tube placed thereunder by the suction pipe vertically moving mechanism 25, so that the sample solution is sucked up into the flow cell 13B and held therein for a while to be heated to the constant temperature. When the measurement for the flow cell 12A has been completed and the sample solution in the flow cell 13B has been heated to the constant temperature, the flow cell 12B is moved and placed on the optical axis 23 by the cell moving mechanism 19 to measure the absorbance changes of the sample solution. During the period of the above measurement, a next sample solution is introduced into the flow cell 12A and heated to the constant temperature.

In this embodiment, the time (about 20 sec.) required to heat the sample solution in one of the flow cells to the constant temperature is made approximately equal to the time (about 20 sec.) required to measure the absorbance changes of the sample solution in the other flow cell. Accordingly, by simultaneously effecting the heating for one flow cell and the absorbance-change measurement for the other flow cell and by alternately effecting the heating and the absorbance-change measurement for each flow cell, many sample solutions can be successively processed at a period which is nearly equal to the sum of the time required to measure the absorbance changes and the time required to change over the flow cells. Moreover, since the flow cells of the same characteristics are readily available, measurements on many sample solutions can be correctly made without being accompanied with errors due to a change in optical path length.

Figure 2:
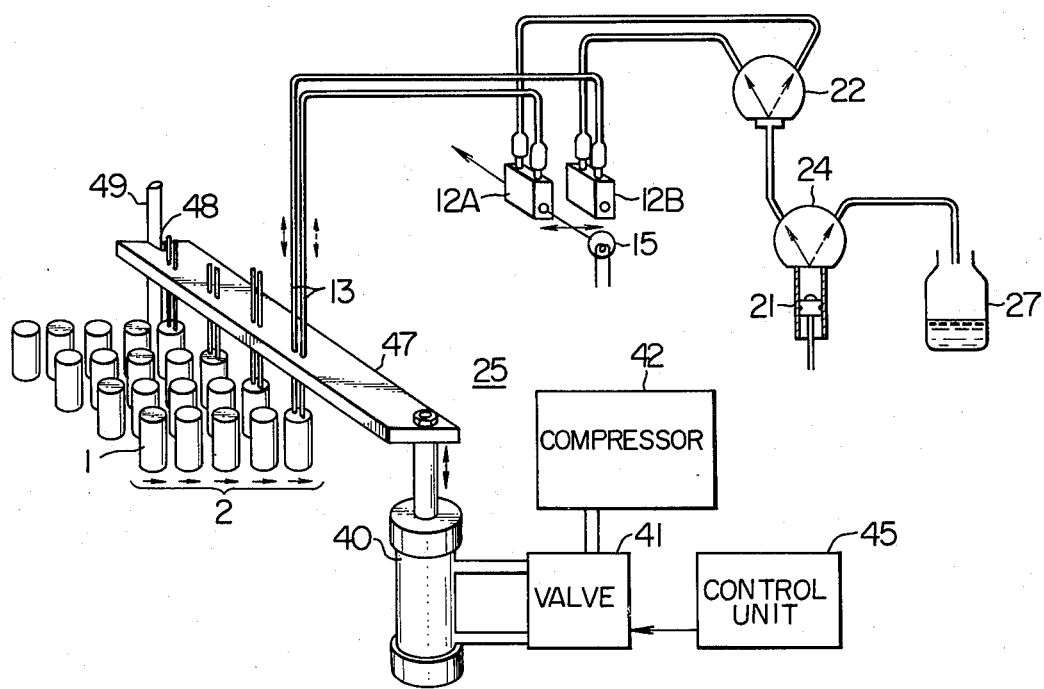
FIG. 2 is a schematic view for explaining the arrangement in the vicinity of the vertical movement mechanism for suction pipe shown in FIG. 1.

FIG. 2 shows the arrangement in the vicinity of the vertical movement mechanism 25 for suction pipe shown in FIG. 1. In FIG. 2 an example is shown in which four trains of reaction tubes 1 are provided in the reaction line 2. When the suction pump 21 formed of a syringe performs the pushing-out operation, the sample solution is discharged from the suction pump 21 to a waste solution tank 27 through the valve 24.

A plurality of suction pipes 13 are mounted on an arm 47. Respective suction pipes 13 communicate with corresponding flow cells. The arm 47 is moved in the vertical direction by an air cylinder 40. When the arm 47 is lowered, the respective lower ends of the suction pipes 13 are inserted into the sample solutions contained in the reaction tubes. A notch 48 is provided in the arm 47 so that it may slide along an auxiliary rod 49. The air cylinder 40 is connected to an electromagnetic valve 41 which is controlled by a control unit 45. The compressed air is supplied from a compressor 42 to the air cylinder 40 through the electromagnetic valve 41, at need.

Figure 3:
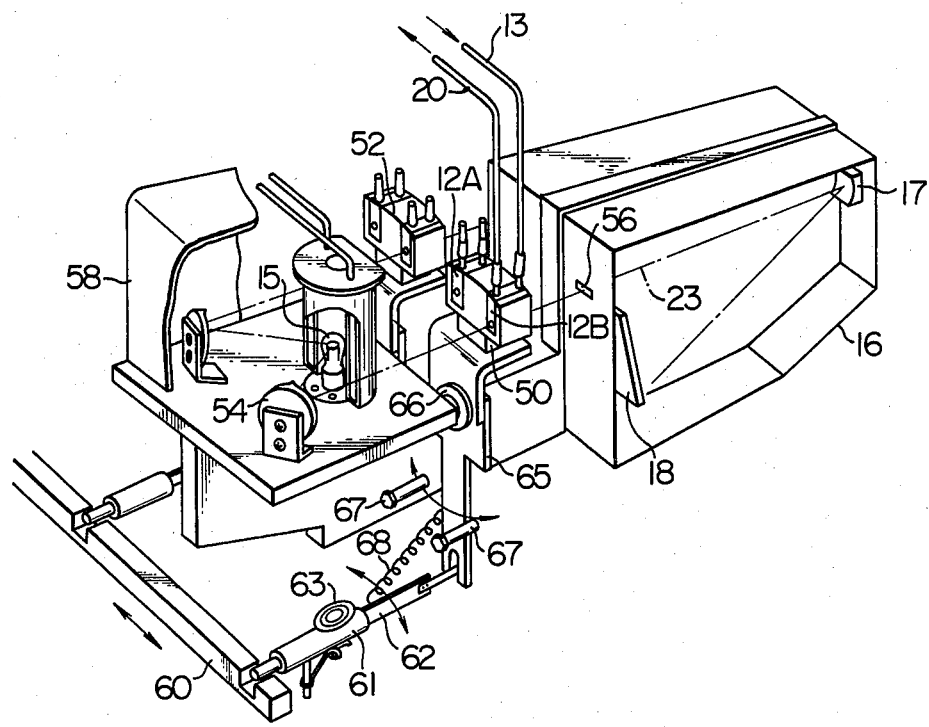
FIG. 3 is a schematic view for explaining the arrangement in the vicinity of the photometer shown in FIG. 1.
Figure 4:
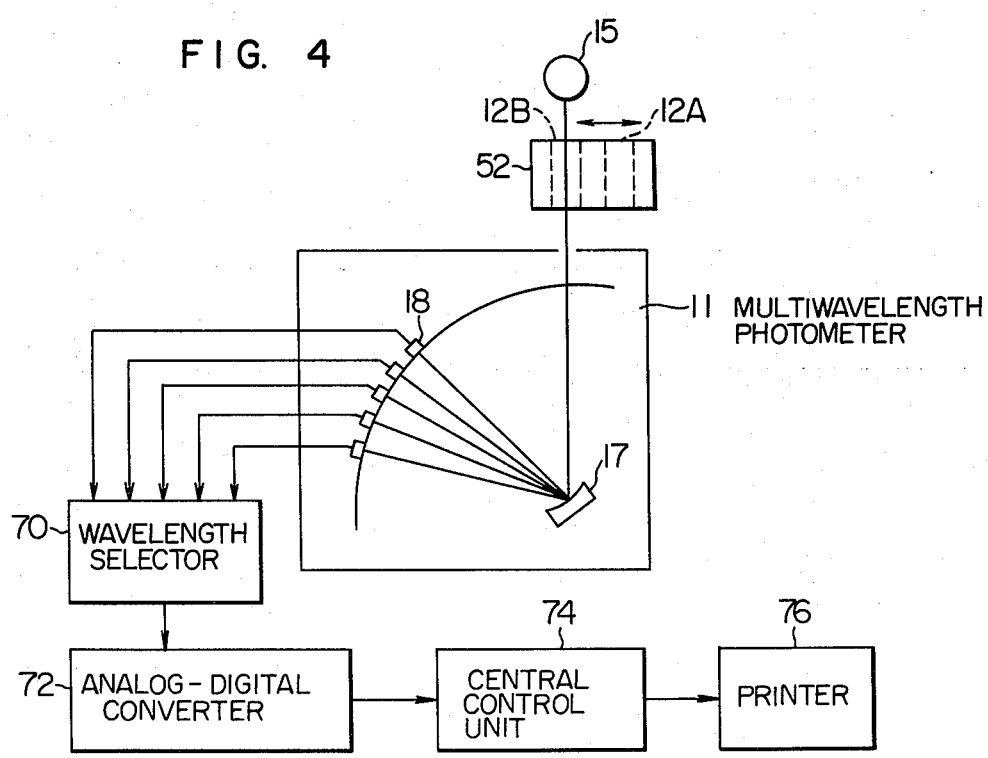
FIG. 4 is an explanatory view of an embodiment of the optical system and the display part of the analizing apparatus shown in FIG. 1.

FIG. 3 shows the arrangement in the vicinity of the photometer 11 shown in FIG. 1. The light source lamp 15 and concave mirrors 54 are enclosed by a light source cover 58. A light beam from the lamp 15 is led into the spectrometer 16 through the concave mirror 54, one of the flow cells 12A and 12B, in this instance the flow cell 12B as shown in FIG. 3, and an entrance slit 56. White light is incident upon the flow cell 12B and the light having passed through the flow cell 12B is dispersed by the grating 17 to detect only specified wavelength components by the detector 18. As shown in FIG. 4, the detector 18 is provided with a plurality of detecting elements which are used to detect signals contained in individual wavelength components corresponding to examination items. That is, a detecting element corresponding to a necessary wavelength component is selected by a wavelength selector 70 to obtain a desired electric signal. In usual use, two wavelength components are taken out of the light having passed through one flow cell. An analog signal delivered from the wavelength selector 70 is converted by an analog-digital converter 72 into a digital signal, which is subject to a predetermined processing in a central control unit 74 so that the active value of the sample with respect to the corresponding examination item may be indicated on a printer 76. The photometer 11 is equipped with the dispersion element 17 in the form of a concave grating to separate the incident light beam into a multiplicity of monochromatic light beams and, therefore, called the multiwavelength photometer.

The flow cells 12A and 12B are mounted on a cell block 52 which is provided at the bottom thereof with a Peltier element 50. The alternate setting of the flow cells 12A and 12B on the optical axis 23 is effected by the movement of a driving lever 60 which is given a reciprocating motion by an air cylinder. In more detail, if the driving lever 60 is displaced to the right, a rotating lever 61 turns about a bearing 63 which is used as the axis of rotation so that a plate spring 62 is moved to the left. The above motion is reinforced by the action of a pull spring 68. Since a supporting plate 65 is rotatable on a bearing 66, the movement of the plate spring 62 to the left or counterclockwise causes the supporting plate 65 to turn counterclockwise to reach a stopper 67. Thus, the cell block 52 is moved to the right so that the flow cell 12A is placed on the optical axis 23. When the flow cell 12B is to be placed on the optical axis, the driving lever 65 is displaced to the left by the air cylinder.

In the aforementioned embodiment, two flow cells are mounted on one cell block. However, in a case where the time required to heat the sample solution sucked up into one flow cell to a constant temperature is longer than the time required to measure the absorbance changes of the sample solution in one flow cell, three or more flow cells are preferably mounted on the cell block. That is, these flow cells are successively used to measure the absorbance changes of the sample solution while the other flow cells than the flow cell which is subject to the absorbance-change measurement are used to heat the respective sample solutions to a constant temperature. Thus, it is possible to prevent the lowering of the processing speed due to a waiting time which is necessary to stabilize the temperature of the sample solution.

As explained hereinbefore, according to the present invention, in measuring the absorbance change of sample solution, many sample solutions can be successively processed without being affected by the waiting time required to stabilize the temperature of sample solutions, and thus the sample processing speed in the rate method can be greatly enhanced.

We claim:

1. An apparatus for an optical rate assay comprising: a train of vessels each containing a sample solution whose optical characteristic is to be measured; a plurality of flow cells;

optical unit means for observing changes in light absorbance of a sample solution in one of said flow cells placed in an optical path;

means for maintaining said respective flow cells at a predetermined temperature while the respective flow cell is placed not only in said optical path but also out of said optical path;

means for selectively introducing, during a period when a sample solution introduced from a specified one of said vessels into a specified one of said flow cells is held in said specified flow cell, a sample solution in a next one of said vessels into a different one of said flow cells;

means for placing said different one of said flow cells at a location out of said optical path when the sample solution is introduced into said different one of said flow cells, and for bringing said different flow cell into said optical path after the sample solution contained in said different flow cell has reached a predetermined temperature by replacing said specified flow cell by said different flow cell;

optical unit means for observing changes in absorbance of said sample solution in said different flow cell by irradiating said sample solution in said different flow cell with light, after changes in absorbance of said sample solution in said specified flow cell has been observed; and means for displaying results of observation corresponding to the respective absorbance changes of said sample solutions in said respective flow cells.

2. An optical rate assay apparatus according to claim 1, wherein said plurality of flow cells are used, in order, to be successively supplied with a sample solution from a corresponding one of said vessels.

3. An optical rate assay apparatus according to claim 1, wherein said sample solution introducing means includes a suction device connected to said flow cells and a pipe capable of being inserted into said vessels.

4. An optical rate assay apparatus according to claim 1, wherein said optical unit means obtains photometric signals resulting from said sample solution in each of said flow cells a plurality of times to measure a reaction rate of said sample solution.

5. An optical rate assay apparatus according to claim 1, wherein said means for maintaining said flow cells at said constant temperature includes a Peltier element.

6. An apparatus for an optical rate assay comprising: means for intermittently transferring a train of vessels, each of said vessels containing therein a sample solution which contains a material to be examined and a reactive reagent;

at least one introducing pipe having an open end for taking in said sample solution contained in each of said vessels at a predetermined position;

a plurality of flow cells;

optical unit means for observing changes in light absorbance of the sample solution in one of said flow cells placed in an optical path;

means for maintaining said respective flow cells at a predetermined temperature while the respective flow cell is placed not only in said optical path but also out of said optical path;

means for inserting said introducing pipe into one of said vessels which is successively transferred to said predetermined position and placed thereat;

means for introducing, during a period when a sample solution introduced from a specified one of said vessels into a specified one of said flow cells is held in said specified flow cell into a different one of said flow cells through said introducing pipe;

means for placing said different one of said flow cells at a location out of said optical path when the sample solution is introduced into said different one of said flow cells, and for bringing said different flow cell into said optical path after the sample solution contained in said different flow cell has reached a predetermined temperature by replacing said specified flow cell by said different flow cell;

optical unit means for irradiating said different flow cell with light, during a period when said sample solution is held in said different flow cell, to observe changes in absorbance of said sample solution in said different flow cell; and means for displaying results of observation corresponding to the respective absorbance changes of said sample solutions in said respective flow cells.

7. An optical rate assay apparatus according to claim 6, wherein said train of vessels are made up of a plurality of vessels connected with each other through a chain and each of said vessels is supplied with said material to be examined and said reactive reagent in the course of the transfer of said train of vessels.

8. An optical rate assay apparatus according to claim 6, wherein each of said flow cells is connected to corresponding one of a plurality of introducing pipes.

9. An optical rate assay apparatus according to claim 6, wherein said flow cells are connected to a single introducing pipe through a change-over valve.

10. An apparatus for an optical rate assay comprising:

a train of vessels each containing a reaction solution in which a sample and a reagent are mixed;

means for moving said train of vessels intermittently at a predetermined interval so as to successively place said respective vessels at a sucking position one after another;

a movable part including a thermally conductive block, at least two, a first and a second, flow cells mounted on said block, and a heat generating source provided on said block;

a photometer for effecting a rate assay with respect to the reaction solution in one of said flow cells placed in an optical path;

a first suction pipe coupled with said first flow cell, for introducing the reaction solution into said first flow cell from one of said vessels which is placed at said sucking position;

a second suction pipe coupled with said second flow cell, for introducing the reaction solution into said second flow cell from another vessel of said train which is placed at said sucking position in succession of the introducing operation by said first suction pipe;

movable part displacing means for successively placing said flow cells of said movable part one after another into an optical path of said photometer, the rate assay with respect to the reaction solution within said first flow cell being effected while said first flow cell is placed in said optical path, the reaction solution sucked by said second suction pipe into said second flow cell, which is placed out of said optical path, being heated while said first flow cell is placed in said optical path;

selection means for selecting one flow cell which is not placed in said photometer optical path and for causing reaction solution to be introduced into said one flow cell; and blockade means for closing a flow path of a specified one of said flow cells so that the reaction solution can not flow through said specified flow cell while the reaction solution introduced into said specified flow cell is heated and while said specified flow cell is placed in said optical path.

* * * * *